US006960452B2

(12) United States Patent
Hubbell et al.

(10) Patent No.: US 6,960,452 B2
(45) Date of Patent: Nov. 1, 2005

(54) ENZYME-MEDIATED MODIFICATION OF FIBRIN FOR TISSUE ENGINEERING: INCORPORATION OF PROTEINS

(75) Inventors: Jeffrey A. Hubbell, Zurich (CH); Jason C. Schense, Zurich (CH); Shelly E. Sakiyama, Zurich (CH)

(73) Assignees: Eidgenossische Technische Hochschule Zurich, Zurich (CH); Universitat Zurich, Zurich (CH)

(*) Notice: Subject to any disclaimer, the term of this patent is extended or adjusted under 35 U.S.C. 154(b) by 489 days.

(21) Appl. No.: 09/798,338

(22) Filed: Mar. 2, 2001

(65) Prior Publication Data

US 2001/0020086 A1 Sep. 6, 2001

Related U.S. Application Data

(63) Continuation of application No. 09/141,153, filed on Aug. 27, 1998, now abandoned.

(51) Int. Cl.[7] .......................... C12P 21/00; A61K 9/14; A01N 1/00
(52) U.S. Cl. ...................... 435/69.7; 435/7.1; 424/484; 424/279.1; 530/300; 530/350; 530/380; 514/2; 514/12; 514/56
(58) Field of Search ............................. 424/484, 279.1; 530/300, 380, 350, 402, 382; 514/2, 56, 12; 435/7.1, 69.7, 2, 69.1, 195, 382

(56) References Cited

U.S. PATENT DOCUMENTS

| | | |
|---|---|---|
| 4,613,665 A | 9/1986 | Larm |
| 4,810,784 A | 3/1989 | Larm |
| 5,100,668 A | 3/1992 | Edelman et al. |
| 5,171,670 A | 12/1992 | Kronenberg et al. |
| 5,202,247 A | 4/1993 | Kilburn et al. |
| 5,504,001 A | 4/1996 | Foster |
| 5,561,982 A | 10/1996 | Tunkel et al. |
| 5,693,341 A | 12/1997 | Schroeder et al. |
| 5,773,577 A | 6/1998 | Capello |
| 5,840,837 A | 11/1998 | Krstenansky et al. |
| 5,877,153 A | 3/1999 | Harris et al. |
| 2002/0146414 A1 * | 10/2002 | Sakiyama-Elbert et al. ............. 424/141.1 |
| 2003/0119186 A1 * | 6/2003 | Hubbell et al. ............. 435/397 |

FOREIGN PATENT DOCUMENTS

WO    WO 92/02620    2/1992

OTHER PUBLICATIONS

Mosher et al., J. Biol. Chem. 255, 1181–1188 (1980).*
Besson, et al., "Synthetic peptide substrates for a conductimetric assay of *Pseudomonas aeruginosa* elastase," *Analytical Biochemistry* 237(0232):216–223 (1996).
Borrajo, et al., "Derivatized Cyclodextrins as peptidometics: Influence on Neurite Growth," *Bioorganic and Medicinal Chemistry Letters* 7:1185–90 (1997).
Coombs, et al. "Directing sequence–specific proteolysis to new targets. The influence of loop size and target sequence on selective proteolysis by tissue–type plasminogen activator and urokinase–type plasminogen activator," *J. Biol. Chem.* 273(8):4323–8 (1998).
Dimilla, et al., "Mathematical model for the effects of adhesion and mechanics on cell migration speed," *Biophys. J.* 60(1):15–37 (1991).
Dinbergs, et al., "Cellular response to transforming growth factor–beta1 and basic fibroblast growth factor depends on release kinetics and extracellular matrix interactions," *J. Biol. Chem.* 271(47):29822–9 (1996).
Edelman, et al., "Basic fibroblast growth factor enhances the coupling of intimal hyperplasia and proliferation of vasa vasorum in injured rat arteries," *J. Clin. Invest.* 89(2):465–73 (1992).
Edelman, et al., "Controlled and modulated release of basic fibroblast growth factor," *Biomaterials.* 12(7):619–26 (1991).
Edelman, et al., "Perivascular and intravenous administration of basic fibroblast growth factor: vascular and solid organ deposition," *Proc. Natl. Acad. Sci. U. S. A.* 90(4):1513–7 (1993).
Edgar, et al., "The heparin–binding domain of laminin is responsible for its effects on neurite outgrowth and neuronal survival," *Embo J.* 3(7):1463–8 (1984).
Götz, et al., "Neurotrophin–6 is a new member of the nerve growth factor family," *Nature* 372(6503):266–9 (1994).
Harada, et al., "Basic fibroblast growth factor improves myocardial function in chronically ischemic porcine hearts," *J. Clin. Invest.* 94(2):623–30 (1994).
Kallapur, et al, "The neural cell adhesion molecule (NCAM) heparin binding domain binds to cell surface heparan sulfate proteoglycans," *J. Neurosci. Res.* 33(4):538–48 (1992).

(Continued)

*Primary Examiner*—Jon Weber
*Assistant Examiner*—Chih-Min Kam
(74) *Attorney, Agent, or Firm*—Pabst Patent Group LLP

(57) ABSTRACT

Disclosed are materials that may be used in the design of improved devices and wound treatment platforms though covalent and/or non-covalent attachment of bioactive proteins. The proteins comprise any variety of cell growth and/or healing promoting proteins, such as growth factor. The incorporation of these whole proteins may be designed to provide controlled release thereof in a biological system through further use of enzyme degradation sites. Heparin-binding protein or fusion proteins synthesized to contain a heparin-binding domain are two mechanisms that may be used in providing these properties to a matrix, such as a fibrinogen matrix. The proteins will be used to provide enhanced healing in various tissues including vasculature, skin, nerve, and liver. The materials disclosed will be used to enhance would?? Healing and other generative processes by engineering the fibrin gel to contain appropriate proteins with specifically designed release and/or degradation characteristics.

10 Claims, 1 Drawing Sheet

OTHER PUBLICATIONS

Kaneda, et al., "Midkine, a heparin–binding growth/differentiation factor, exhibits nerve cell adhesion and guidance activity for neurite outgrowth in vitro," *J. Biochem.* 119(6):1150–6 (1996).

Kleinman, et al., "The laminins: a family of basement membrane glycoproteins important in cell differentiation and tumor metastases," *Vitam. Horm.* 47:161–86 (1993).

Hata, et al., "Binding of lipoprotein lipase to heparin. Identification of five critical residues in two distinct segments of the amino–terminal domain," *J. Biol. Chem.* 268(12):8447–57 (1993).

Haugen, et al, "Central and peripheral neurite outgrowth differs in preference for heparin–binding versus integrin–binding sequences," *J. Neurosci.* 12(6):2034–42 (1992).

Herbert, et al., "Effects of fibinolysis on neurite growth from dorsal root ganglia cultured in two– and three–dimensional fibrin gels," *J. Comp. Neurol.* 365(3):380–91 (1996).

Herbert, et al., "Effects of fibrin micromorphology on neurite growth from dorsal root ganglia cultured in three–dimensional fibrin gels," *J. Biomed. Mater. Res.* 40(4):551–9 (1998).

Kallapur, et al, "The neural cell adhesion molecule (NCAM) heparin binding domain binds to cell surface heparan sulfate proteoglycans," *J. Neurosci. Res.* 33(4):538–48 (1992).

Kaneda, et al., "Midkine, a heparin–binding growth/differentiation factor, exhibits nerve cell adhesion and guidance activity for neurite outgrowth in vitro," *J. Biochem.* 119(6):1150–6 (1996).

Kiguchi, et al., "Altered expression of epidermal growth factor receptor ligands in tumor promoter–treated mouse epidermis and in primary mouse skin tumors induced by an initiation–promotion protocol," *Mol. Carcinog.* 22(2):73–83 (1998).

Kinosaki, et al., "Identification of heparin–binding stretches of a naturally occurring deleted variant of hepatocyte growth factor (dHGF)," *Biochim. Biophys. Acta.* 1384(1):93–102 (1998).

Lopez, et al., "Basic fibroblast growth factor in a porcine model of chronic myocardial ischemia: a comparison of angiographic, echocardiographic and coronary flow parameters," *J. Pharmacol. Exp. Ther.* 282(1):385–90 (1997).

Lopez, et al., "Local perivascular administration of basic fibroblast growth factor: drug delivery and toxicological evaluation," *Drug Metab. Dispos.* 24(8):922–4 (1996).

Martin & Timpl, "Laminin and other basement membrane components," *Annu. Rev. Cell. Biol.* 3:57–85 (1987).

Massia, et al., "An RGD spacing of 440 nm is sufficient for integrin alpha V beta 3–mediated fibroblast spreading and 140 nm for focal contact and stress fiber formation," *J. Cell. Biol.* 114(5):1089–100 (1991).

McCaffrey, et al., "Transforming growth factor–beta 1 is a heparin–binding protein: identification of putative heparin–binding regions and isolation of heparins with varying affinity for TGF–beta 1," *J. Cell. Physiol.* 152(2):430–40 (1992).

Netzel–Arnett, et al., "Sequence specificities of human fibroblast and neutrophil collagenases," *J. Biol. Chem.* 266(11):6747–55 (1991).

Nolo, et al., "Developmentally regulated neurite outgrowth response from dorsal root ganglion neurons to heparin–binding growth–associated molecule (HB–GAM) and the expression of HB–GAM in the targets of the developing dorsal root ganglion neurites," *Eur. J. Neurosci.* 8(8):1658–65 (1996).

Presta, et al., "Structure–function relationship of basic fibroblast growth factor: site–directed mutagenesis of a putative heparin–binding and receptor–binding region," *Biochem. Biophys. Res. Commun.* 185(3):1098–107 (1992).

Rogers, et al., "Neuron–specific interactions with two neurite–promoting fragments of fibronectin," *J. Neurosci.* 5(2):369–78 (1985).

Sellke, et al., "Basic FGF enhances endothelium–dependent relaxation of the collateral–perfused coronary microcirculation," *Am. J. Physiol.* 267(4 Pt 2):H1303–11 (1994).

Smith, et al., "Rapid identification of highly active and selective substrates for stromelysin and matrilysin using bacteriophage peptide display libraries," *J. Biol. Chem.* 270(12):6440–9 (1995).

Spillman, et al., "Defining the interleukin–8–binding domain of heparan sulfate," *J. Biol. Chem.* 273(25):15487–93 (1998).

Steffen, et al., "Characterization of cell–associated and soluble forms of connective tissue growth factor (CTGF) produced by fibroblast cells in vitro," *Growth Factors* 15(3):199–213 (1998).

Studier, et al., "Use of T7 RNA polymerase to direct expression of cloned genes," *Methods Enzymol.* 185:60–89 (1990).

Takagi, et al., "Amino acid sequence studies on the alpha chain of human fibrinogen. Location of four plasmin attack points and a covalent cross–linking site," *Biochemistry* 14(23):5149–56 (1975).

Tashiro, et al., "A synthetic peptide containing the IKVAV sequence from the A chain of laminin mediates cell attachment, migration, and neurite outgrowth," *J. Biol. Chem.* 264(27):16174–82 (1989).

Tessler, et al., "Heparin modulates the interaction of VEGF165 with soluble and cell associated flk–1 receptors," *J. Biol. Chem.* 269(17):12456–61 (1994).

Tyler–Cross, et al., "Heparin binding domain peptides of antithrombin III: analysis by isothermal titration calorimetry and circular dichroism spectroscopy," *Protein Sci.* 3(4):620–7 (1994).

Yamada, "Adhesive recognition sequences," *J. Biol. Chem.* 266(20):12809–12 (1991).

Yanish–Perron, et al., "Improved M13 phage cloning vectors and host strains: nucleotide sequences of the M13mp18 and pUC19 vectors," *Gene.* 33(1):103–19 (1985).

Zucker & Katz, "Platelet factor 4: production, structure, and physiologic and immunologic action," *Proc. Soc. Exp. Biol. Med.* 198(2):693–702 (1991).

\* cited by examiner

US 6,960,452 B2

ENZYME-MEDIATED MODIFICATION OF FIBRIN FOR TISSUE ENGINEERING: INCORPORATION OF PROTEINS

This application is a continuation of U.S. application Ser. No. 09/141,153 filed Aug. 27, 1998, now abandoned.

FIELD OF THE INVENTION

The present invention relates generally to the fields of matrices that are modified to enclose particularly designed fusion proteins. More particularly, it concerns the use of fusion proteins that include internal degradation sites and/or enzymatic cleavage sites. Artificial matrices may be designed having desired degradation rates, as well as to include particular active biological molecules, such as growth factors or enzymes.

BACKGROUND OF THE INVENTION

It has been demonstrated that bi-domain peptides, which contain a factor XIIIa substrate sequence and a bioactive peptide sequence, can be cross-linked into fibrin gels and furthermore, that this bioactive peptide retains its cellular activity in vitro. While peptides can partially mimic the bioactivity of the whole protein from which they are derived, this bioactivity is usually lower than the bioactivity of the whole protein, and sometimes it is impossible to mimic certain proteins with only a short peptide. In order to incorporate the specific bioactivity of these types of factors, such as growth factors, it would be beneficial for the entire protein to be incorporated into the fibrin matrix.

SUMMARY OF THE INVENTION

Whole proteins can be incorporated into fibrin gels in a number of ways as taught in this invention. One method is to attach heparin to the gel by either covalent or noncovalent methods. This permits heparin-binding proteins including heparin-binding growth factors to be noncovalently bound to the fibrin gel. If the protein to be bound does not contain a native heparin-binding sequence, a fusion protein can be constructed containing the native protein sequence and a synthetic heparin-binding domain. Alternatively, a fusion protein can be constructed which contains a factor XIIIa substrate and the native protein sequence and this fusion protein can be sequestered by cross-linking it to the gel with factor XIIIa.

Fusion Protein Synthesis

Synthesis of either of the fusion proteins described above can be accomplished by utilizing molecular biology techniques. To do this, a fusion protein can be created that contains the entire protein sequence of interest with a cross-linking or binding sequence fused onto the amino or carboxyl terminus. This is done at the DNA level, as sequences encoding for either a factor XIIIa cross-linking substrate or a heparin-binding domain can be inserted at the beginning or the end of the codons for the original protein. When these modified proteins are expressed, they will then contain the additional domain of interest at the amino terminus. By using the natural machinery designed for protein synthesis, it becomes possible to synthesize and purify large proteins with high fidelity.

Incorporation of Fusion Proteins

Once the protein is purified, it can then be incorporated into the fibrin gels using several different schemes. In the first design, a factor XIIIa substrate has been directly incorporated onto the protein. When this modified protein is present during the polymerization of the fibrin, it is directly incorporated into the fibrin matrix in a manner similar to the bi-domain peptides previously demonstrated (Zucker, M, et al, (1991). *Experimental Biology and Medicine.* 693–702). A separate method involves fusion proteins that have been synthesized with a heparin-binding domain. In this example, a bi-domain peptide, heparin, and the heparin-binding fusion protein are included in the fibrin polymerization mixture. During polymerization, the bi-domain peptide is cross-linked into the fibrin gel. This bi-domain peptide would contain a factor XIIIa substrate sequence in addition to a heparin-binding sequence. The heparin binds to the bi-domain peptide that has been incorporated in the fibrin gel and is trapped in the fibrin matrix. This entrapped heparin serves to sequester the heparin-binding fusion protein within the fibrin gel by binding to the engineered heparin-binding domains. This incorporation has been shown to be stable enough to sequester the growth factor until the cross-linked peptide is removed from the gel via cell controlled proteolysis.

This technique can be further modified by incorporating an enzymatic degradation site between the factor XIIIa substrate sequence and the sequence encoding the protein of interest. By careful selection of $K_m$ and $k_{cat}$ of this enzymatic degradation site, degradation could be controlled to occur either before or after the protein matrix and/or by utilizing similar or dissimilar enzymes to degrade the matrix, with the placement of the degradation site being tailored for each type of protein and application. This new protein could be directly cross-linked into the fibrin matrix as described above. However, incorporating an enzymatic degradation site alters the release of the protein during proteolysis. When the cell-derived proteases reach the sequestered protein, they can cleave the engineered protein at the newly formed degradation site. The resulting degradation products would include the liberated protein, which would now be free of any engineered fusion sequences, as well as any degraded fibrin. Therefore, the free protein would now be identical in primary sequence to the native growth factor and potentially more bioactive. A similar method can be used with the heparin-binding fusion proteins. These new proteins would then contain the protease degradation site, as well as the new heparin-binding domain. The heparin-binding fusion proteins will be sequestered into the matrix by the incorporation of heparin into the fibrin via the covalent immobilization of heparin-binding peptides. Once again, with the new protease degradation site added, the released protein would be identical in primary sequence to the natural protein.

1. Modification of Growth Factors to Provide Synthetic Heparin-binding Domains.

Using standard molecular biology techniques, fusion proteins can be made of any growth factor for which the protein or DNA sequence is known, allowing the addition of novel domains such as heparin-binding domains or enzymatic substrates. These fusion proteins can be constructed so as to add a novel domain to either the N or C-terminus of the protein. The modifications are made at the DNA level by constructing a gene containing both the DNA sequence coding for the growth factor and the DNA sequence coding for a heparin-binding domain. This DNA is then ligated into an expression plasmid and transformed into bacteria. Upon induction of expression, the bacteria will produce large amounts of this fusion protein. Following expression, the protein must be purified from the cell lysate and refolded. Purification is often simplified due to the tendency of mammalian proteins expressed at high levels to form inclusion bodies in bacteria.

The simplest way to incorporate proteins into fibrin is to attach heparin to the fibrin gels and use the heparin to sequester heparin-binding proteins, such as heparin-binding growth factors. This can be accomplished one of two ways, either by directly coupling a heparin-peptide chimera (where the heparin is chemically attached to a peptide containing a factor XIIIa substrate), or indirectly by cross-linking a heparin-binding peptide into the fibrin gel and binding heparin to this peptide non-covalently (using a bifunctional peptide containing a heparin-binding domain and a factor XIIIa substrate). This heparin can then sequester proteins, such as growth factors with heparin affinity, in the fibrin gel in a manner similar to the way that they are sequestered to the extracellular matrix in nature. Heparin can also protect these factors from proteolytic degradation and prolong their activity until they are released from the matrix.

Despite their relatively strong affinity for heparin, heparin-binding growth factors dissociate from the matrix on a short time scale. Therefore, a high excess of binding sites is essential to ensure that they do not diffuse far before they bind to the matrix again. This equilibrium also allows for the binding of free growth factor to cell surface receptors that are in close proximity to the site of dissociation. This method of controlled release provides both relatively long-term binding of growth factors and rapid release of growth factors to local cells.

Heparin-binding domains naturally occur in many different families of growth factors. One of these families with one or more members that bind heparin are the fibroblast growth factors (Presta, M., et al, (1992). *Biochemical and Biophysical Research Communications.* 185:1098–1107). Additional growth factors which bind heparin include transforming growth factor, interleukin-8, neurotrophin-6, vascular endothelial cell growth factor, heparin-binding epidermal growth factor, hepatocyte growth factor, connective tissue growth factor, midkine, and heparin-binding growth associated molecule (Götz, R., et al, (1994). *Nature.* 372:266–269; Kaneda, N., et al, (1996). *Journal of Biochemistry.* 119:1150–1156; Kiguchi, K., et al, (1998). *Molecular Carcinogensis.* 22:73–83; Kinosaki, M., et al, (1998). *Biochimica Biophysica Acta.* 1384:93–102; McCaffrey, T., et al, (1992). *Journal of Cellular Physiology.* 152:430–440; Nolo, R., et al, (1996). *European Journal of Neuroscience.* 8:1658–1665; Spillmann, D., et al, (1998). *Journal of Biological Chemistry.* 273:15487–15493; Steffen, C., et al, (1998). Characterization of cell-associated and soluble forms of connective tissue growth factor (CTGF) produced by fibroblast cells in vitro. *Growth Factors.* 15:199–213; Tessler, S., et al, (1994). *Journal of Biological Chemistry.* 269:12456–12461). These factors have shown the potential to enhance healing in many different types of tissue including vasculature, skin, nerve and liver. Therefore, these materials could be used to enhance wound healing in many different parts of the body by selecting the appropriate growth factor.

2. Approach 1: Heparin-binding Domain-factor XIIIa Substrate+Heparin to Attach Growth Factor The attachment of heparin, either covalently or non-covalently to fibrin gels adds a novel functionality to these materials. The attachment of heparin permits the fibrin matrix to bind heparin-binding proteins, including growth factors in a manner which does not harm the protein, and prevents free diffusion of the protein from the gel. This allows for the controlled-release of heparin-binding proteins by one of two mechanisms, either degradation of the gel or binding of the protein to some other high affinity protein, such as a cell surface receptor.

Heparin can be attached to fibrin gels non-covalently using a two-part system consisting of a peptide chimera and heparin itself. The peptide chimera consists of two domains, a factor XIIIa substrate and a polysaccharide-binding domain. Once the peptide chimera is cross-linked into the fibrin gel, it attaches the heparin (or other polysaccharides) by non-covalent interactions.

Numerous proteins have been found to have heparin-binding affinity. Some of these proteins and the sequences of their heparin-binding domains are listed below.

TABLE 1

Heparin-binding sequences

| Protein | Heparin-binding domain | Reference |
| --- | --- | --- |
| Anti-thrombin III | K(βA)FAKLAARLYRKA (SEQ ID NO:1) | Tyler-Cross, R., et al, (1994) Protein Science 3:620–627 |
| Platelet Factor 4 | YKKIIKKL (SEQ ID NO:2) | Zucker and Katz, 1991 (14) |
| Neural Cell Adhesion Molecule | KHKGRDVILKKDVR (SEQ ID NO:3) | Kallapur, et al, 1992 J Neurosci Res 33:538–548 |
| Fibronectin | YEKPGSPPREVVPRPRPCV (SEQ ID NO:4) KNNQKSEPLIGRKKT (SEQ ID NO:5) | Haugen, et al, 1992 J Neurosci Res 12:2034–2042 |
| bFGF (basic fibroblast growth factor) | KDPKRL (SEQ ID NO: 6) YRSRKY (SEQ ID NO:7) | SwissPROT: P09038 |
| aFGF (acidic fibroblast growth factor) | YKKPKL (SEQ ID NO:8) | SwissPROT: P095230 |
| LPL (lipoprotein lipase) | AKRSSKM (SEQ ID NO:9) CRKRCN (SEQ ID NO:10) | Hata, et al, 1993 J Biol Chem 268:8447–8457 |

Cross-linking Protocol for Use of Heparin-Binding Peptides:
1) Dialyze fibrinogen (8 mg/ml) versus 4 L of Tris buffered saline (33 mM Tris), pH 7.4 for 24 hours.
2) Sterile filter fibrinogen using a 0.2 μm syringe filter.
3) Make the following peptide solutions:

|  | Peptide (25 mg/ml) | heparin (45 mg/ml) | BFGF (5 μg/ml) | Tris buffered saline (TBS) |
| --- | --- | --- | --- | --- |
| Fibrin | 0:1 | 0:1 | 0 μl | 980 μl |
| Peptide | 70:1 | 0:1 | 0 μl | 910 μl |
| Peptide + heparin | 70:1 | 70:1 | 0 μl | 840 μl |
| Peptide + heparin + bFGF | 70:1 | 70:1 | 56 μl | 784 μl |

4) Make thrombin solution: 100 units in 5 ml TBS.
5) Add 1.4 ml of fibrinogen to each peptide solution.
6) Make gels: Add 20 μl of TBS+50 mM CaCl$_2$, 40 μl of thrombin solution (20 units/ml), and 340 μl of peptide solution+fibrinogen. (above solutions make 6 gels).
7) Incubate at 37° C. for 1 hr.
8) Wash 5 times in 24 hours. Use 1 ml of TBS the first 4 times and neuronal media the last time.
9) Dissect day 8 chick embryonic dorsal root ganglia.
10) Place one ganglia in each gel and place at 37° C. for 1 hr.
11) Add 1 ml of neuronal media to each gel.
12) Change media after 24 hours.

These results show that the heparin and peptide alone do not increase neurite extension. When added without peptide and heparin, bFGF does not enhance neurite outgrowth, demonstrating that the washing protocol used is sufficient. Neurite enhancement is increased by the addition of both 1 μg/ml and 5 μg/ml of bound bFGF in a dose dependent manner. The addition of 1.0 μg/ml bound VEGF did not increase neurite extension, suggesting chat the effect from bFGF is not due to its ability to promote angiogenesis.

3. Approach 2: Polysaccharide Grafts (Heparin—Factor XIIIa Substrate Chimera) to Bind Growth Factor Heparin (or other polysaccharides such as heparin sulfate or chondroitin sulfate) can be attached to fibrinogen directly using factor XIIIa by constructing a heparin-peptide chimera. This chimera contains two domains, a peptide domain consisting of a factor XIIIa substrate and the polysaccharide domain, such as heparin. These chimeras are made using modified heparin (or another polysaccharide) which contains a unique reactive group at one end to control the site where coupling occurs on the heparin molecule. Through the use of a unique functional group on the peptide, such as a side chain present only on the end of the peptide where coupling is desired, the location of coupling on the peptide can be controlled as well. These chimeras can then be covalently cross-linked to fibrin gels using the sample methods as peptide chimeras, allowing direct attachment of heparin to the fibrin gel.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
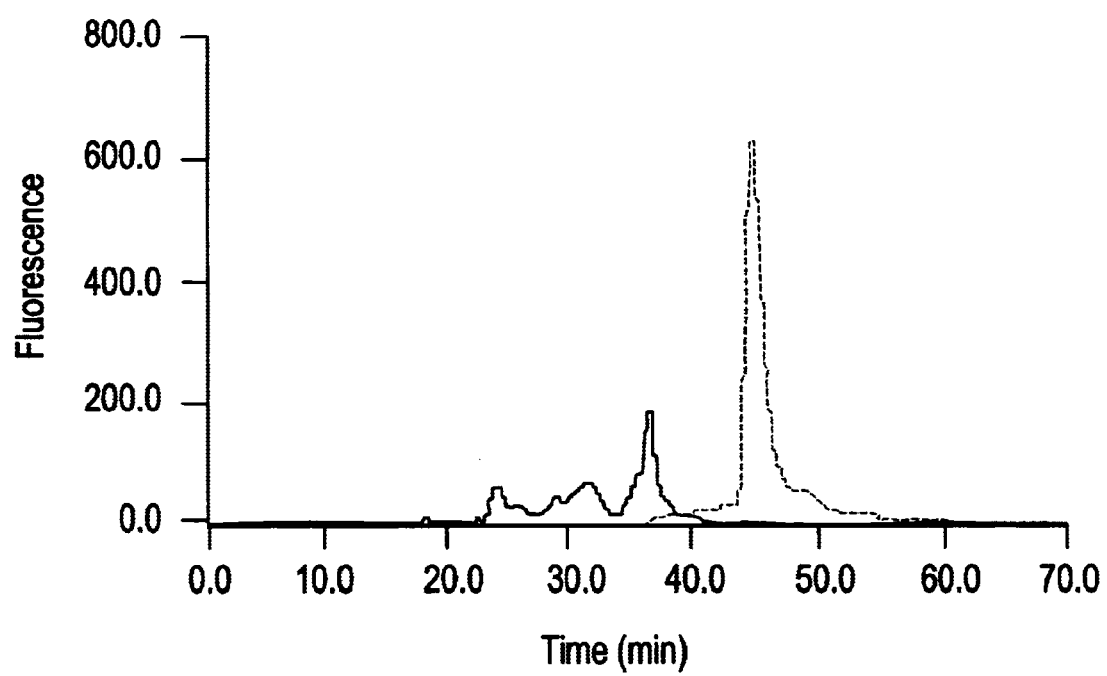
FIG. 1. Fluorescence detection chromatograms of plasmin-degraded peptide-containing fibrin gels and free peptide. Size exclusion chromatography of a degraded fibrin gel with the peptide dLNQEQVSPK (μA) FALAARLYRKA-NH$_2$ (SEQ ID NO:11) incorporated and with the same peptide free (--), not cross-linked into the fibrin, are shown. The free peptide eluted at longer times, corresponding to a lower molecular weight, than the peptide incorporated into the fibrin gel during coagulation, demonstrating covalent incorporation though Factor XIIIa activity.

Following long-standing patent law convention, the terms "a" and "an" mean "one or more" when used in this application, including the claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Indirect Coupling of Heparin Via a Heparin-binding Peptide to Attach Growth Factor A peptide chimera containing both a factor XIIIa substrate and a heparin-binding domain is synthesized by standard solid phase synthesis. A sample peptide is one containing the following sequence, dLNQEQVSPK(βA) FAKLAARLYRKA (SEQ ID NO:12), where the N-terminus of the peptide contains the factor XIIIa substrate and the sequence in italics contains a modified peptide from the heparin-binding domain of ATIII (dL denotes dansyl leucine, which is used to allow detection of the peptide by fluorescence).

Size exclusion chromatography was used to determine the amount of peptide cross-linked to fibrin gels using the previously developed incorporation method. A bi-domain peptide containing the heparin-binding domain from anti-thrombin III and a fluorescent label was incorporated into fibrin gels during polymerization. The free peptide was washed from the gels, and the fibrin network was degraded with plasmin. The degradation products were analyzed by high performance liquid chromatography (size exclusion chromatography) to determine the amount of peptide (by fluorescence) present per mole of fibrinogen (by UV absorbance). The fluorescence signal from peptide-modified gels appeared at an earlier elution time than did the signal from free peptide alone, indicating that all peptide present in the modified gels was cross-linked to fibrin (FIG. 1). Quantification based on standards of known concentration for both peptide and fibrin networks degraded with plasmin showed incorporation of 8.7±0.2 moles of peptide per mole of fibrinogen (n=10), which is in close agreement with previously published results for a peptide containing the same factor XIIIa substrate domain but a vastly different carboxy terminal sequence.

Example 2

Synthesis of Heparin-peptide Chimeras

A heparin-peptide chimera is synthesized by coupling a peptide, containing the factor XIIIa substrate on the N-terminus and a poly-lysine on the C-terminus, to a heparin oligosaccharide, with a unique aldehyde group on one end, via reductive amination. A peptide with the following sequence, dLNQEQVSPLKKKG (SEQ ID NO:13), is synthesized by standard solid phase peptide chemistry. The heparin oligosaccharides are made by standard nitrous acid degradation of heparin, resulting in the formation of an aldehyde on the reducing terminal of the cleaved oligosaccharide. During coupling, the ε-amino group of the lysine side chain attacks the aldehyde on the reducing end of the heparin oligosaccharide to form a Schiff base. The Schiff base is then reduced to form a stable product. A sample coupling protocol is given below.

Coupling Protocol:
1) Dissolve 1.8 mM of peptide and 1.8 mM of nitrous acid degraded heparin in 50 mM borate buffer, pH 9. React for 30 minutes.
2) Add 160 mM NaCNBH$_3$ and react for 12 hours.
3) Add 240 mM NaCNBH$_3$ and react for 12 hours.
4) Adjust pH to 7 with dilute HCl.
5) Add NaCl to a final concentration of 1M.
6) Dialyze versus 4L of deionized water for 24 hours.
7) Lyophilize to obtain reaction product.
8) Analyze reaction yield by size exclusion chromatography.
9) Purification of desired product is accomplished using anion exchange chromatography.

Use: Cross-linking Protocol for Use of Heparin-Peptide Chimeras:
1) Dialyze fibrinogen (8 mg/ml) versus 4 L of Tris buffered saline (33 mM Tris), pH 7.4 for 24 hours.
2) Sterile filter fibrinogen using a 0.2 μm syringe filter.
3) Make the following chimera solutions:

|  | heparin-peptide chimera (67 mg/ml) | bFGF (5 g/ml) | Tris buffered saline (TBS) |
| --- | --- | --- | --- |
| Fibrin | 0 μl | 0 μl | 980 μl |
| heparin-peptide chimera | 70 μl | 0 μl | 840 μl |
| heparin-peptide chimera + bFGF | 70 μl | 56 μl | 784 μl |

4) Make thrombin solution: 100 units in 5 ml TBS.
5) Add 1.4 ml of fibrinogen to each chimera solution.
6) Make gels: Add 20 μl of TBS+50 mM CaCl$_2$, 40 μl of thrombin solution (20 units/ml), and 340 μl of chimera solution+fibrinogen. (above solutions make 6 gels).
7) Incubate at 37° C. for 1 hr.
8) Wash 5 times in 24 hours. Use 1 ml of TBS the first 4 times and neuronal media the last time.
9) Dissect day 8 chick embryonic dorsal root ganglia.
10) Place one ganglia in each gel and place at 37° C. for 1 hr.
11) Add 1 ml of neuronal media to each gel.
12) Change media after 24 hours.

Example 3

Degradable Sites in Fusion Protein and in Peptide Chimera

Fusion proteins or peptide chimeras, which are cross-linked to fibrin gels, may be further modified to contain a degradable site between the attachment site (i.e., factor XIIIa substrate or heparin-binding domain) and the bioactive protein (i.e., growth factor or enzyme). These sites may be degradable either by non-specific hydrolysis (i.e., an ester bond) or they may be substrates for specific enzymatic (either proteolytic or polysaccharide degrading) degradation. These degradable sites allow the engineering of more specific release of bioactive factor from fibrin gels. For example, degradation based on enzymatic activity allows for the release of bioactive factors to be controlled by a cellular process rather than by diffusion of the factor through the gel.

The degradation sites allow the bioactive factor to be released with little or no modification to the primary protein sequence, which may result in higher activity of the factor. In addition, it allows the release of the factor to be controlled by cell specific processes, such as localized proteolysis, rather than diffusion from some porous materials. This allows factors to be released at different rates within the same material depending on the location of cells within the material. Cell specific proteolytic activity is vital in applications such as nerve regeneration, which occur over long periods of time. This also reduces the amount of total growth factor needed, since its release is controlled by cellular processes. Conservation of growth factor and its bioavailability are distinct advantages of exploiting cell specific proteolytic activity over the use of diffusion controlled release devices which characteristically result in the loss of a significant amount of bioactive factor in an initial burst release.

Enzymes that could be used for proteolytic degradation are numerous. Proteolytically degradable sites could include substrates for collagenase, plasmin, elastase, stromelysin, or plasminogen activators. Exemplary substrates are listed below. P1–P5 denote amino acids 1–5 positions toward the amino terminus of the protein from the site where proteolysis occurs. P1'–P4' denote amino acids 1–4 positions toward the carboxy terminus of the protein from the site where proteolysis occurs.

TABLE 2

Sample substrate sequences for protease.

| Protease | P5 | P4 | P3 | P2 | P1 | P1' | P2' | P3' | P4' | SEQ ID NO: | Reference |
| --- | --- | --- | --- | --- | --- | --- | --- | --- | --- | --- | --- |
| Plasmin |  |  |  | L | I | K | M | K | P | SEQ ID NO: 22 | Takagi, T. et al, (1975). Biochemistry 14:5149–5156 |
| Plasmin |  |  |  | N | F | K | S | Q | L | SEQ ID NO: 23 | Takagi, T. et al, (1975) Biochemistry 14:5149–5156 |
| Stromelysin | Ac | G | P | L | A | L | T | A | L | SEQ ID NO: 24 | Smith, M. M. et al. (1995) 1995 270:6440–6449 |
| Stromelysin |  | Ac | P | F | E | L | R | A | NH$_2$ | SEQ ID NO: 25 | Smith, M. M. et al. (1995) 1995 270:6440–6449 |
| Elastase |  |  | Z— | A | A | F | A | NH$_2$ |  | SEQ ID NO: 26 | Besson, C. et al (1996) Analytical Biochemistry 237:216–223 |

TABLE 2-continued

Sample substrate sequences for protease.

| Protease | P5 | P4 | P3 | P2 | P1 | P1' | P2' | P3' | P4' | SEQ ID NO: | Reference |
|---|---|---|---|---|---|---|---|---|---|---|---|
| Collagenase | | G | P | L | G | I | A | G | P | SEQ ID NO: 27 | Netzel-Arnett et al (1991) Journal of Biological Chemistry 266:6747–6755 |
| t-PA | P | H | Y | G | R | S | G | G | | SEQ ID NO: 28 | Coombs, G. S. et al. 1998 Journal of Biological Chemistry 273:4323–4328 |
| u-PA | P | G | S | G | R | S | A | S | G | SEQ ID NO: 29 | Coombs, G. S. et al. 1998. Journal of Biological Chemistry 273:4323–4328 |

Enzymatic degradation can occur with polysaccharide substrates for enzymes such as heparinase, heparitinase, and chondroitinase ABC. Each of these enzymes have polysaccharide substrates. By virtue of the presence of heparin in all of the heparin-binding, systems, the substrate for heparinase is already built into these systems.

Non-enzymatic degradation substrate can consist of any linkage which undergoes hydrolysis by an acid or base catalyzed mechanism. These substrates can include oligo-esters such as oligomers of lactic or glycolic acid. The rate of degradation of these materials can be controlled through the choice of oligomer.

b) Substrates with Heparin, Plasmin Sites, or Oligo-ester Polysaccharide Substrates Polysaccharide degradation substrate can be included in either of the embodiments, Approach 1 or 2, through the use of heparin in either system. This provides a substrate for heparinase to degrade. It could degrade either the heparin present in the heparin-peptide chimera (Approach 2). Or, it could degrade the heparin in the non-covalent heparin-peptide complex (Approach 1).

Proteolytic Substrates

Proteolytic substrate could be added during the peptide synthesis of either the peptide chimera or the heparin-peptide chimera. The heparin-binding peptide chimera could be modified to contain a proteolytic degradation sequence by inserting a protease substrate, such as one of the ones for plasmin described above, between the factor XIIIa substrate and the heparin-binding domain. The heparin-peptide chimera could be modified to contain a proteolytic degradation sequence by inserting a protease substrate, such as one of the ones for plasmin described above, between the factor XIIIa substrate and the heparin domain. A substrate with a high $K_m$ and a low $k_{cat}$ could be used to slow cleavage while occupying active sites of the protease. The cleavage substrates other than those for plasmin could be used to allow release of the bioactive factors to be independent of matrix degradation.

Oligo-esters

An oligo-ester substrate could be inserted between the factor XIIIa substrate and either the heparin-binding domain or the heparin domain of the chimera during the peptide synthesis step as well. This could be accomplished using a oligo-ester such as oligomers of lactic acid.

Example 4

Fusion Proteins Together with Growth Factors that do not Bind Heparin Spontaneously In order to sequester growth factors which do not spontaneously bind heparin, it is necessary to modify the protein through the addition of a functionality capable of attaching to fibrin. This can be accomplished in several ways. By way of example, this may be achieved through the addition of a factor XIIIa substrate or by adding a heparin-binding domain to the resulting fusion protein.

a) Addition of a Factor XIIIa Substrate

The addition of a synthetic factor XIIIa substrate can be accomplished by expressing a fusion protein containing the native growth factor sequence and a factor XIIIa substrate at either the amino or carboxyl terminus of the fusion protein. This modification is done at the DNA level. Whole proteins present difficulty in that they are synthesized by solid phase chemical synthesis. The DNA sequence encoding the growth factor is adapted to optimal codon usage for bacterial expression. The DNA sequence is then determined for the desired Factor XIIIa substrate, using codons which occur frequently in bacterial DNA.

A series of gene fragments is designed prior to the DNA synthesis. Due to the error frequency of most DNA synthesis, which contains an error approximately every 50 bp, genes are constructed to be approximately 100 bp in length. This reduces the number of colonies that must be screened in order to find one containing the proper DNA sequence. The location at which one gene ends and the next begins is selected based on the natural occurrence of unique restriction enzyme cut sites within the gene, resulting in fragments (or oligonucleotides) of variable length. The process is greatly assisted by the use of software which identifies the location and frequency of restriction enzyme sites within a given DNA sequence.

Once the gene fragments have been successfully designed, common restriction enzyme sites are included on the ends of each fragment to allow ligation of each fragment into a cloning plasmid. For example, adding tcoRI and HindIII sites to each gene fragment allows it to be inserted into the polylinker cloning region of pUC 19 (Yanish-Perron, C., et al, (1985). *Gene.* 33:103–119). The 3' and 5' single strands of each gene fragment are then synthesized using standard solid phase synthesis with the proper sticky ends for insertion into the cloning vector. Following cleavage and desalting, the single stranded fragments are then purified by PAGE and annealed. After phosphorylation, the annealed fragments are ligated into a cloning vector, such as pUC 19.

Following ligation, the plasmids are transformed into DH5-F' competent cells and plated on Isopropyl-D-Thiogalactopyranoside(IPTG)/5-Bromo-4-chloro-3-indolyl-D-Galactopyranoside (X-gal) plates to screen for the insertion of the gene fragments. The resulting colonies which contain gene fragment are then screened for insertion of the proper length. This is accomplished by purifying plasmid from colonies of transformed cells by alkaline lysis miniprep protocol and digesting the plasmid with the restriction enzyme sites present at either end of the gene fragment. Upon detection of the fragments of the proper length by agarose gel electrophoresis, the plasmids are sequenced.

When a plasmid containing a gene fragment with the proper sequence is identified, the fragment is then cut out and used to assemble the full gene. Each time one plasmid is cut with the enzymes at the insertion points and purified from an agarose gel after dephosphorylation of the plasmid. Meanwhile, a second plasmid containing the fragment to be inserted is also cut and the fragment to be inserted is purified from an agarose gel. The insert DNA is then ligated into the dephosphorylated plasmid. This process is continued until the full gene is assembled. The gene is then moved into an expression vector, such as pET 14b (Studier, F., et al, (1990). *Methods in Enzymology.* 185:60–89) and transformed into bacteria for expression. After this final ligation, the full gene is sequenced to confirm that it is correct.

Expression of the fusion protein is accomplished by growing the bacteria until they reach mid-log phase growth and then inducing expression of the fusion protein. Expression is continued for approximately 3 hours and the cells are then harvested. After obtaining a bacterial cell pellet, the cells are lysed. The cell membranes and debris are removed by washing the cell lysate pellet with Triton X100, leaving the inclusion bodies in relatively pure form. The fusion protein is solubilized using high urea concentrations and purified by histidine affinity chromatography. The resulting protein is then renatured gradually by dialysis against a slowly decreasing amount of urea and lyophilized.

Example 5

Addition of a Heparin-Binding Domain Directly to Growth Factor Protein

The addition of a synthetic heparin-binding domain can be accomplished by expressing a fusion protein containing the native growth factor sequence and heparin-binding domain at either the amino or carboxyl terminus of the fusion protein. This modification is done at the DNA level. The DNA sequence encoding the growth factor is adapted to optimal codon usage for bacterial expression. The DNA sequence is then determined for the desired heparin-binding domain, using bacterial codons.

A series of gene fragments is then constructed and assembly of the full gene is performed as described above for a factor XIIIa substrate. Once the full gene is assembled, it is moved to an expression plasmid and the fusion protein is synthesized as described above. This protein is purified as described above for the factor XIIIa substrate fusion protein.

Example 6

Fusion Protein with a Degradable Site

A fusion protein containing either the factor XIIIa substrate or the heparin-binding domain can be synthesized with a degradable site between the native growth factor sequence and "cross-linking" functionality. This may be accomplished by modification of the DNA sequence. The gene is designed and assembled as described above.

Example 7

Biosynthesis of Factor XIIIA Substrate Fusion Protein with NGF

NGF can be expressed as fusion protein in *E. coli*, which contains a factor XIIIa substrate at the N-terminus and the human β-NGF sequence at the C-terminus of the protein. This is accomplished by constructing a synthetic gene containing the DNA which codes for the desired fusion protein. The protein sequence to be expressed is as follows:

(SEQ ID NO:14)
*MGSSHHHHHHSSGLVPRGSHM*NQEQVSPLPVELESSSHPIFHRGEFSVCD
SVSVWVGDKTTATDIKGKEVMVLGEVNINNSVFKQYFFETKCRDPNPV
DSGCRGIDSKHWNSYCTTTHTFVKALTMDGKQAAWRFIRIDTACVCVL
SRKAVRZ, where the region in italics is the Histidine tag derived from the expression vector, and the underlined region is the thrombin cleavage site. The residues are the cross-linking substrate sequence for factor XIIIa.

The cloning plasmid used for gene assembly was pUC 18, which is the same as pUC 19 except that the sequence of the polylinker cloning region is reversed. A map of pUC 19 follows, which was obtained from New England Biolabs. The DNA sequence of the gene is as follows from 5' to 3':

(SEQ ID NO:15)
GAATTCCATATGAACCAGGAACAGGTTAGCCCGCTGCCCGTGGAACT
CGAGAGCTCTTCCCACCCGATTTTCCATCGTGGCGAGTTCTCCGTGTG
TGACTCTGTCTCTGTATGGGTAGGCGATAAAACCACTGCCACTGATA
TCAAAGGCAAAGAGGTGATGGTGCTGGGAGAAGTAAACATTAACAA
CTCTGTATTCAAACAGTACTTCTTCGAAACTAAGTGCCGTGACCCGA
ACCCGGTAGACTCTGGGTGTCGCGGCATCGATTCTAAACACTGGAAC
TCTTACTGCACCACTACTCACACTTTCGTTAAAGCGTTGACTATGGAT
GGTAAACAGGCTGCCTGGCGTTTCATCCGTATCGATACTGCATGCGT
GTGTGTACTGTCCCGTAAAGCTGTTCGTTAAGGATCC.

This gene is inserted between the EcoRI and HindIII sites in the polylinker cloning region of pUC 18, as shown in the map.

After gene assembly, this gene is inserted into the expression vector pET 14b between the Nde1 and BamHI sites. A map of the pET 14b vector follows, which was obtained from Novagen. After insertion of the gene into the expression vector, the plasmid is transformed into BL21 (DE3) pLysS competent cells. The cells are grown until they reach an O.D. of about 0.6, then they are induced to express the fusion protein with IPTG (final concentration in solution 0.4 mM). Expression is continued for 2–3 hours. The cells are placed on ice for 5 minutes and then harvested by centrifugation at 5000×g for 5 min. at 4° C. They are resuspended in 0.25 culture volume of cold 50 mM Tris-HCl pH 8.0 at 25° C. The cells are centrifuged as before and the pellet is frozen. Cells are lysed upon thawing.

The cell lysate is centrifuged and the supernatant discarded. The pellet is resuspended in Triton X100. The solution is then centrifuged and the supernatant is discarded. The pellet is resuspended in 6M urea and the fusion protein is purified by histidine affinity chromatography. The histidine tag can be cleaved by thrombin during polymerization and washed from the gels during the standard washing procedure.

b) Biosynthesis of Heparin-binding Domain Fusion Proteins

NGF can be expressed as fusion protein in *E. coli*, which contains a heparin-binding domain at the N-terminus and the NGF sequence at the C-terminus of the protein. This is accomplished by constructing a synthetic gene containing the DNA which codes for the desired fusion protein. The protein sequence to be expressed is as follows:

(SEQ ID NO:16)
*MGSSHHHHHHSSGLVPRGS*HMKDPKRLYRSRKLPVELESSSHPIFHRGE
FSVCDSVSVWVGDKTTATDIKGKEVMVLGEVNINNSVFKQYFFETKCRD
PNPVDSGCRGIDSKHWNSYCTTTHTFVKALTMDGKQAAWRFIRIDTAC
VCVLSRKAVRZ, where the region in italics is the Histidine tag derived from the expression vector, and the underlined region is the thrombin cleavage site. The region underlined with a dotted underline is the heparin-binding sequence.

The cloning plasmid used for gene assembly was pUC 18. The DNA sequence of the gene is as follows from 5' to 3':

(SEQ ID NO:17)
GAATTCCCATGGCATATGAAAGACCCGAAACGTCTGTACCGTTCTCG
TAAACTGCCCGTGGAACTCGAGAGCTCTTCCCACCCGATTTTCCATCG
TGGCGAGTTCTCCGTGTGTGACTCTGTCTCTGTATGGGTAGGCGATAA
AACCACTGCCACTGATATCAAAGGCAAAGAGGTGATGGTGCTGGGA
GAAGTAAACATTAACAACTCTGTATTCAAACAGTACTTCTTCGAAAC
TAAGTGCCGTGACCCGAACCCGGTAGACTCTGGGTGTCGCGGCATCG
ATTCTAAACACTGGAACTCTTACTGCACCACTACTCACACTTTCGTTA
AAGCGTTGACTATGGATGGTAAACAGGCTGCCTGGCGTTTCATCCGT
ATCGATACTGCATGCGTGTGTGTACTGTCCCGTAAAGCTGTTCGTTAA
GGATCC.

This gene is inserted between the EcoRI and HindIII sites in the polylinker-cloning region of pUC 18, as shown in the map.

After assembly this gene is inserted into the expression vector. Expression and purification are then performed as described above.

Example 8

Fusion Protein with Degradable Site
Factor XIIIa Substrate with Plasmin Site

NGF can be expressed as fusion protein in *E. coli*, which contains a factor XIIIa substrate at the N-terminus, a plasmin substrate in the middle, and the NGF sequence at the C-terminus of the protein. This is accomplished by constructing a synthetic gene containing the DNA which codes for the desired fusion protein. The protein sequence to be expressed is as follows:

(SEQ ID NO:18)
*MGSSHHHHHHSSGLVPRGS*HMNQEQVSPLPVELPLIKMKPVELESSSHPI
FHRGEFSVCDSVSVWVGDKTTATDIKGKEVMVLGEVNINNSVFKQYFFET
KCRDPNPVDSGCRGIDSKHWNSYCTTTHTFVKALTMDGKQAAWRFIR
IDTACVCVLSRKAVRZ, where the region in italics is the Histidine tag derived from the expression vector, and the underlined region is the thrombin cleavage site. The residues are the cross-linking substrate sequence for factor XIIIa, and double underlined region denotes the plasmin substrate.

The cloning plasmid used for gene assembly was pUC 18. The DNA sequence of the gene is as follows from 5' to 3':

(SEQ ID NO:19)
GAATTCCCATGGCATATGAACCAGGAACAGGTTAGCCCGCTGCCCGT
GGAACTGCCGCTGATCAAAATGAAACCCGTGGAACTCGAGAGCTCTT
CCCACCCGATTTTCCATCGTGGCGAGTTCTCCGTGTGTGACTCTGTCT
CTGTATGGGTAGGCGATAAAACCACTGCCACTGATATCAAAGGCAAA
GAGGTGATGGTGCTGGGAGAAGTAAACATTAACAACTCTGTATTCAA
ACAGTACTTCTTCGAAACTAAGTGCCGTGACCCGAACCCGGTAGACT
CTGGGTGTCGCGGCATCGATTCTAAACACTGGAACTCTTACTGCACC
ACTACTCACACTTTCGTTAAAGCGTTGACTATGGATGGTAAACAGGC
TGCCTGGCGTTTCATCCGTATCGATACTGCATGCGTGTGTGTACTGTC
CCGTAAAGCTGTTCGTTAAGGATCC.

This gene is inserted between the EcoRI and HindIII sites in the polylinker cloning region of pUC 18, as shown in the map.

After assembly this gene is inserted into the expression vector. Expression and purification are then performed as described above.

Heparin-binding with Plasmin Site

NGF can be expressed as fusion protein in *E. coli*, which contains a heparin-binding domain at the N-terminus, a plasmin substrate in the middle and the NGF sequence at the C-terminus of the protein. This is accomplished by constructing a synthetic gene containing the DNA which codes for the desired fusion protein. The protein sequence to be expressed is as follows:

(SEQ ID NO:20)
*MGSSHHHHHHSSGLVPRGS*HMKDPKRLYRSRKLPVELPLIKMKPVELES
SSHPIFHRGEFSVCDSVSVWVGDKTTATDIKGKEVMVLGEVNINNSVFKQ
YFFETKCRDPNPVDSGCRGIDSKHWNSYCTTTHTFVKALTMDGKQAAW
RFIRIDTACVCVLSRKAVRZ, where the region in italics is the Histidine tag derived from the expression vector, and the underlined region is the thrombin cleavage site. Dotted underline denote the heparin-binding sequence, and double underline denotes the plasmin substrate.

The cloning plasmid used for gene assembly was pUC 18. The DNA sequence of the gene is as follows from 5' to 3':

(SEQ ID NO:21)
GAATTCCCATGGCATATGAAAGACCCGAAACGTCTGTACCGTTCTCG
TAAACTGCCCGTGGAACTGCCGCTGATCAAAATGAAACCCGTGGAAC
TCGAGAGCTCTTCCCACCCGATTTTCCATCGTGGCGAGTTCTCCGTGT
GTGACTCTGTCTCTGTATGGGTAGGCGATAAAACCACTGCCACTGAT
ATCAAAGGCAAAGAGGTGATGGTGCTGGGAGAAGTAAACATTAACA
ACTCTGTATTCAAACAGTACTTCTTCGAAACTAAGTGCCGTGACCCG
AACCCGGTAGACTCTGGGTGTCGCGGCATCGATTCTAAACACTGGAA
CTCTTACTGCACCACTACTCACACTTTCGTTAAAGCGTTGACTATGGA
TGGTAAACAGGCTGCCTGGCGTTTCATCCGTATCGATACTGCATGCG
TGTGTGTACTGTCCCGTAAAGCTGTTCGTTAAGGATCC.

This gene is inserted between the EcoRI and HindIII sites in the polylinker cloning region of pUC 18, as shown in the map.

After assembly this gene is inserted into the expression vector. Expression and purification are then performed as described above.

REFERENCES

The following references, to the extent that they provide exemplary procedural or other details supplementary to those set forth herein, are specifically incorporated herein by reference.

1. Besson, C., et al, (1996). *Analytical Biochemistry.* 237:216–223.
2. Coombs, G. S., et al, 1998. *Journal of Biological Chemistry.* 273:4323–4328.
3. Götz, R., et al, (1994). *Naure.* 372:266–269.
4. Hata, A., et al, (1993). *Journal of Biological Chemistry.* 268:8447–8457.
5. Haugen, P., et al, (1992). *Journal of Neuroscience.* 12:2034–2042.
6. Kallapur, S., et al, (1992). *Journal of Neuroscience Research.* 33:538–548.
7. Kaneda, N., et al, (1996). *Journal of Biochemistry.* 119:1150–1156.
8. Kiguchi, K., et al, (1998). *Molecular Carcinogensis.* 22:73–83.
9. Kinosaki, M., et al,(1998). *Biochimica Biophysica Acta.* 1384:93–102.
10. McCaffrey, T., et al, (1992). *Journal of Cellular Physiology.* 152:430–440.
11. Netzel-Arnett, et al, (1991). *Journal of Biological Chemistry.* 266:6747–6755.

12. Nolo, R., et al, (1996). *European Journal of Neuroscience.* 8:1658–1665.
13. Presta, M., et al, (1992). *Biochemical and Biophysical Research Communications.* 185:1098–1107.
14. Zucker, M, et al, (1991). *Experimental Biology and Medicine.* 693–702.
15. Smith, M. M., et al, (1995). 1995. 270:6440–6449.
16. Spillmann, D., et al, (1998). *Journal of Biological Chemistry.* 273:15487–15493.
17. Steffen, C., et al, (1998). Characterization of cell-associated and soluble forms of connective tissue growth factor (CTGF) produced by fibroblast cells in vitro. *Growth Factors.* 15:199–213.
18. Studier, F., et al, (1990). *Methods in Enzymology.* 185:60–89.
19. Takagi, T., et al, (1975). *Biochemistry.* 14:5149–5156.
20. Tessler, S., et al, (1994). *Journal of Biological Chemistry.* 269:12456–12461.
21. Tyler-Cross, R., et al, (1994). *Protein Science.* 3:620–627.
22. Yanish-Perron, C., et al, (1985). *Gene.* 33:103–119.

What is claimed is:

1. A matrix comprising fibrin, a peptide comprising a domain that binds with heparin or heparin-like compounds and a factor XIIIa substrate domain, heparin or a heparin-like compound, and a heparin binding growth factor, wherein the peptide is covalently attached to the fibrin through the factor XIIIa substrate domain.

2. The matrix of claim 1 wherein the heparin binding growth factor is a protein with at least two domains, wherein one domain binds heparin or a heparin-like compounds and one domain is a growth factor.

3. The matrix of claim 2 wherein the heparin binding growth factor is selected from the group consisting of a natural heparin binding growth factor and a recombinant growth factor.

4. The matrix of claim 2 wherein the heparin binding growth factor is a recombinant growth factor expressed as a fusion protein which comprises a heparin binding domain and a growth factor domain.

5. The matrix of claim 4 wherein the heparin binding domain is not directly attached to the growth factor domain of the fusion protein.

6. The matrix of claim 5 wherein the heparin binding growth factor further comprises a protease cleavage site between the recombinant growth factor and the heparin binding domain.

7. A method of making a matrix for the controlled delivery of growth factor, comprising adding a peptide to a fibrin matrix, wherein the peptide comprises a domain that binds with heparin and a factor XIIIa substrate domain;

coupling the factor XIIa substrate domain to the fibrin matrix;

adding to the fibrin matrix a heparin or a heparin-like compound; and adding to the fibrin matrix a heparin binding growth factor.

8. A chimeric peptide comprising a domain that binds heparin or heparin-like compounds and a factor XIIIa substrate domain.

9. The peptide of claim 8, wherein the domain that binds heparin or heparin-like compounds is the heparin-binding domain in a compound selected from the group consisting of Anti-thrombin III, Platelet Factor 4, Neural Cell Adhesion Molecule, Fibronectin, basic fibroblast growth factor, acidic fibroblast growth factor, and lipoprotein lipase.

10. The peptide of claim 8, wherein the peptide has the sequence of dLNQEQVSPK(A)FAKLAARLYRKA (SEQ ID NO:12).

* * * * *

UNITED STATES PATENT AND TRADEMARK OFFICE
CERTIFICATE OF CORRECTION

| | | |
|---|---|---|
| PATENT NO. | : 6,960,452 B2 | Page 1 of 2 |
| APPLICATION NO. | : 09/798338 | |
| DATED | : November 1, 2005 | |
| INVENTOR(S) | : Jeffery A. Hubbell, Jason C. Schense and Shelley E. Sakiyama | |

It is certified that error appears in the above-identified patent and that said Letters Patent is hereby corrected as shown below:

Title page,
Item [57], ABSTRACT,
Line 2, "though" should be -- through --;
Line 5, "factor" should be -- factors --;
Line 15, "would?? Healing" should be -- wound healing --.

Column 1,
Line 24, "in vitro" should be italicized.

Column 4,
Line 19, "Zucker and Katz, 1991" should be -- Zucker, M, et al., 1991 Proc. Soc. Exp. Biol. Med. 198(2):639-702--;
Line 20, "(14)" should be deleted;
Line 66, "these" should be -- the --.

Column 5,
Line 6, "neunite" should be -- neurite -- and "chat" should be -- that --;
Line 29, "drawings form" should be -- drawing forms --;
Line 30, "are" should be -- is --;
Line 31, "one or more of these" should be -- this -- and "drawings" should be -- drawing --;
Line 38, "LNQEQVSPK" should be italicized and "(µA)" should be -- (ßA) --.

Column 6,
Line 20, "K(ßA)" should be italicized;
Line 21, "FAKLAARLYRKA" should be italicized.

Column 9,
Line 21, the comma "," after "heparin-binding" should be deleted;
Line 60, "an" should be -- a --.

Column 11,
Line 1, "fragment" should be -- fragments --.

Column 12,
Line 6, "LVPRGS" should be underlined with a single solid line.

UNITED STATES PATENT AND TRADEMARK OFFICE
CERTIFICATE OF CORRECTION

PATENT NO. : 6,960,452 B2
APPLICATION NO. : 09/798338
DATED : November 1, 2005
INVENTOR(S) : Jeffery A. Hubbell, Jason C. Schense and Shelley E. Sakiyama It is certified that error appears in the above-identified patent and that said Letters Patent is hereby corrected as shown below:

Column 13,
Line 1, "LVPRGS" should be underlined with a single solid line, and "KDPKRLYRSRKLP" should be underlined with a dotted line;
Line 42, "LVPRGS" should be underlined with a single solid line and "LIKMK" should be underlined with two solid lines.

Column 14,
Line 12, "LVPRGS" should be underlined with a single solid line, "KDPKRLYRSRKLP" should be underlined with a dotted line and "LIKMK" should be underlined with two solid lines.

Column 29,
Line 31, "compounds" should be -- compound --.

Column 30,
Line 26, "XIIA" should be -- XIIIA --.

Signed and Sealed this

Eleventh Day of July, 2006

JON W. DUDAS
*Director of the United States Patent and Trademark Office*

```
                              SEQUENCE LISTING

<160> NUMBER OF SEQ ID NOS: 29

<210> SEQ ID NO 1
<211> LENGTH: 14
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: beta Alanine

<400> SEQUENCE: 1

Lys Ala Phe Ala Lys Leu Ala Ala Arg Leu Tyr Arg Lys Ala
1               5                   10

<210> SEQ ID NO 2
<211> LENGTH: 8
<212> TYPE: PRT
<213> ORGANISM: Homo sapiens

<400> SEQUENCE: 2

Tyr Lys Lys Ile Ile Lys Lys Leu
1               5

<210> SEQ ID NO 3
<211> LENGTH: 14
<212> TYPE: PRT
<213> ORGANISM: Homo sapiens

<400> SEQUENCE: 3

Lys His Lys Gly Arg Asp Val Ile Leu Lys Lys Asp Val Arg
1               5                   10

<210> SEQ ID NO 4
<211> LENGTH: 19
<212> TYPE: PRT
<213> ORGANISM: Homo sapiens

<400> SEQUENCE: 4

Tyr Glu Lys Pro Gly Ser Pro Pro Arg Glu Val Val Pro Arg Pro Arg
1               5                   10                  15

Pro Cys Val

<210> SEQ ID NO 5
<211> LENGTH: 15
<212> TYPE: PRT
<213> ORGANISM: Homo sapiens

<400> SEQUENCE: 5

Lys Asn Asn Gln Lys Ser Glu Pro Leu Ile Gly Arg Lys Lys Thr
1               5                   10                  15
```

```
<210> SEQ ID NO 6
<211> LENGTH: 6
<212> TYPE: PRT
<213> ORGANISM: Homo sapiens

<400> SEQUENCE: 6

Lys Asp Pro Lys Arg Leu
1               5

<210> SEQ ID NO 7
<211> LENGTH: 6
<212> TYPE: PRT
<213> ORGANISM: Homo sapiens

<400> SEQUENCE: 7

Tyr Arg Ser Arg Lys Tyr
1               5

<210> SEQ ID NO 8
<211> LENGTH: 6
<212> TYPE: PRT
<213> ORGANISM: Homo sapiens

<400> SEQUENCE: 8

Tyr Lys Lys Pro Lys Leu
1               5

<210> SEQ ID NO 9
<211> LENGTH: 7
<212> TYPE: PRT
<213> ORGANISM: Homo sapiens

<400> SEQUENCE: 9

Ala Lys Arg Ser Ser Lys Met
1               5

<210> SEQ ID NO 10
<211> LENGTH: 6
<212> TYPE: PRT
<213> ORGANISM: Homo sapiens

<400> SEQUENCE: 10

Cys Arg Lys Arg Cys Asn
1               5

<210> SEQ ID NO 11
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: dansyl Leucine
<220> FEATURE:
<221> NAME/KEY: MISC_FEATURE
<222> LOCATION: (10)..(10)
<223> OTHER INFORMATION: beta Alanine
<220> FEATURE:
<221> NAME/KEY: MOD_RES
<222> LOCATION: (21)..(21)
<223> OTHER INFORMATION: AMIDATION

<400> SEQUENCE: 11

Leu Asn Gln Glu Gln Val Ser Pro Lys Ala Phe Ala Leu Ala Ala Arg
1               5                   10                  15
```

Leu Tyr Arg Lys Ala
                20

<210> SEQ ID NO 12
<211> LENGTH: 22
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: dansyl Leucine
<220> FEATURE:
<221> NAME/KEY: MISC_FEATURE
<222> LOCATION: (10)..(10)
<223> OTHER INFORMATION: beta Alanine

<400> SEQUENCE: 12

Leu Asn Gln Glu Gln Val Ser Pro Lys Ala Phe Ala Lys Leu Ala Ala
1               5                   10                  15

Arg Leu Tyr Arg Lys Ala
                20

<210> SEQ ID NO 13
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: dansyl Leucine

<400> SEQUENCE: 13

Leu Asn Gln Glu Gln Val Ser Pro Leu Lys Lys Lys Gly
1               5                   10

<210> SEQ ID NO 14
<211> LENGTH: 153
<212> TYPE: PRT
<213> ORGANISM: Artificial sequence
<220> FEATURE:
<223> OTHER INFORMATION: Fusion protein

<400> SEQUENCE: 14

Met Gly Ser Ser His His His His His His Ser Ser Gly Leu Val Pro
1               5                   10                  15

Arg Gly Ser His Met Asn Gln Glu Gln Val Ser Pro Leu Pro Val Glu
                20                  25                  30

Leu Glu Ser Ser Ser His Pro Ile Phe His Arg Gly Glu Phe Ser Val
                35                  40                  45

Cys Asp Ser Val Ser Val Trp Val Gly Asp Lys Thr Thr Ala Thr Asp
        50                  55                  60

Ile Lys Gly Lys Glu Val Met Val Leu Gly Glu Val Asn Ile Asn Asn
65                  70                  75                  80

Ser Val Phe Lys Gln Tyr Phe Phe Glu Thr Lys Cys Arg Asp Pro Asn
                85                  90                  95

Pro Val Asp Ser Gly Cys Arg Gly Ile Asp Ser Lys His Trp Asn Ser
                100                 105                 110

Tyr Cys Thr Thr Thr His Thr Phe Val Lys Ala Leu Thr Met Asp Gly
                115                 120                 125

Lys Gln Ala Ala Trp Arg Phe Ile Arg Ile Asp Thr Ala Cys Val Cys
        130                 135                 140

Val Leu Ser Arg Lys Ala Val Arg Glx
145                 150

<210> SEQ ID NO 15
<211> LENGTH: 414
<212> TYPE: DNA
<213> ORGANISM: Artificial sequence
<220> FEATURE:
<223> OTHER INFORMATION: Nucleotide sequence encoding fusion protein

<400> SEQUENCE: 15

| | | |
|---|---|---|
| gaattccata tgaaccagga acaggttagc ccgctgcccg tggaactcga gagctcttcc | 60 |
| cacccgattt ccatcgtgg cgagttctcc gtgtgtgact ctgtctctgt atgggtaggc | 120 |
| gataaaacca ctgccactga tatcaaaggc aaagaggtga tggtgctggg agaagtaaac | 180 |
| attaacaact ctgtattcaa acagtacttc ttcgaaacta agtgccgtga cccgaacccg | 240 |
| gtagactctg ggtgtcgcgg catcgattct aaacactgga actcttactg caccactact | 300 |
| cacactttcg ttaaagcgtt gactatggat ggtaaacagg ctgcctggcg tttcatccgt | 360 |
| atcgatactg catgcgtgtg tgtactgtcc cgtaaagctg ttcgttaagg atcc | 414 |

<210> SEQ ID NO 16
<211> LENGTH: 157
<212> TYPE: PRT
<213> ORGANISM: Artificial sequence
<220> FEATURE:
<223> OTHER INFORMATION: Fusion protein

<400> SEQUENCE: 16

Met Gly Ser Ser His His His His His Ser Ser Gly Leu Val Pro
1               5                   10                  15

Arg Gly Ser His Met Lys Asp Pro Lys Arg Leu Tyr Arg Ser Arg Lys
            20                  25                  30

Leu Pro Val Glu Leu Glu Ser Ser His Pro Ile Phe His Arg Gly
        35                  40                  45

Glu Phe Ser Val Cys Asp Ser Val Ser Val Trp Val Gly Asp Lys Thr
    50                  55                  60

Thr Ala Thr Asp Ile Lys Gly Lys Glu Val Met Val Leu Gly Glu Val
65                  70                  75                  80

Asn Ile Asn Asn Ser Val Phe Lys Gln Tyr Phe Phe Glu Thr Lys Cys
                85                  90                  95

Arg Asp Pro Asn Pro Val Asp Ser Gly Cys Arg Gly Ile Asp Ser Lys
            100                 105                 110

His Trp Asn Ser Tyr Cys Thr Thr Thr His Thr Phe Val Lys Ala Leu
        115                 120                 125

Thr Met Asp Gly Lys Gln Ala Ala Trp Arg Phe Ile Arg Ile Asp Thr
    130                 135                 140

Ala Cys Val Cys Val Leu Ser Arg Lys Ala Val Arg Glx
145                 150                 155

<210> SEQ ID NO 17
<211> LENGTH: 432
<212> TYPE: DNA
<213> ORGANISM: Artificial sequence
<220> FEATURE:
<223> OTHER INFORMATION: Nucleotide sequence encoding fusion protein.

<400> SEQUENCE: 17

| | | |
|---|---|---|
| gaattcccat ggcatatgaa agacccgaaa cgtctgtacc gttctcgtaa actgccgtg | 60 |
| gaactcgaga gctcttccca cccgattttc atcgtggcg agttctccgt gtgtgactct | 120 |

```
gtctctgtat gggtaggcga taaaaccact gccactgata tcaaaggcaa agaggtgatg      180
gtgctgggag aagtaaacat taacaactct gtattcaaac agtacttctt cgaaactaag      240
tgccgtgacc cgaacccggt agactctggg tgtcgcggca tcgattctaa acactggaac      300
tcttactgca ccactactca cactttcgtt aaagcgttga ctatggatgg taaacaggct      360
gcctggcgtt tcatccgtat cgatactgca tgcgtgtgtg tactgtcccg taaagctgtt      420
cgttaaggat cc                                                          432

<210> SEQ ID NO 18
<211> LENGTH: 163
<212> TYPE: PRT
<213> ORGANISM: Artificial sequence
<220> FEATURE:
<223> OTHER INFORMATION: Fusion Protein

<400> SEQUENCE: 18

Met Gly Ser Ser His His His His His Ser Ser Gly Leu Val Pro
1               5                  10                  15

Arg Gly Ser His Met Asn Gln Glu Gln Val Ser Pro Leu Pro Val Glu
            20                  25                  30

Leu Pro Leu Ile Lys Met Lys Pro Val Glu Leu Glu Ser Ser His
        35                  40                  45

Pro Ile Phe His Arg Gly Glu Phe Ser Val Cys Asp Ser Val Ser Val
    50                  55                  60

Trp Val Gly Asp Lys Thr Thr Ala Thr Asp Ile Lys Gly Lys Glu Val
65                  70                  75                  80

Met Val Leu Gly Glu Val Asn Ile Asn Asn Ser Val Phe Lys Gln Tyr
                85                  90                  95

Phe Phe Glu Thr Lys Cys Arg Asp Pro Asn Pro Val Asp Ser Gly Cys
            100                 105                 110

Arg Gly Ile Asp Ser Lys His Trp Asn Ser Tyr Cys Thr Thr Thr His
        115                 120                 125

Thr Phe Val Lys Ala Leu Thr Met Asp Gly Lys Gln Ala Ala Trp Arg
    130                 135                 140

Phe Ile Arg Ile Asp Thr Ala Cys Val Cys Val Leu Ser Arg Lys Ala
145                 150                 155                 160

Val Arg Glx

<210> SEQ ID NO 19
<211> LENGTH: 450
<212> TYPE: DNA
<213> ORGANISM: Artificial sequence
<220> FEATURE:
<223> OTHER INFORMATION: Nucleotide sequence encoding fusion protein

<400> SEQUENCE: 19
gaattcccat ggcatatgaa ccaggaacag gttagcccgc tgcccgtgga actgccgctg       60
atcaaaatga acccgtggaa actcgagagc tcttcccacc cgattttcca tcgtggcgag      120
ttctccgtgt gtgactctgt ctctgtatgg gtaggcgata aaaccactgc cactgatatc      180
aaaggcaaag aggtgatggt gctgggagaa gtaaacatta acaactctgt attcaaacag      240
tacttcttcg aaactaagtg ccgtgacccg aacccggtag actctgggtg tcgcggcatc      300
gattctaaac actggaactc ttactgcacc actactcaca ctttcgttaa agcgttgact      360
atggatggta acaggctgcc ctggcgtttc atccgtatcg atactgcatg cgtgtgtgta      420
ctgtcccgta aagctgttcg ttaaggatcc                                       450
```

```
<210> SEQ ID NO 20
<211> LENGTH: 167
<212> TYPE: PRT
<213> ORGANISM: Artificial sequence
<220> FEATURE:
<223> OTHER INFORMATION: Fusion protein

<400> SEQUENCE: 20

Met Gly Ser Ser His His His His His His Ser Ser Gly Leu Val Pro
1               5                   10                  15

Arg Gly Ser His Met Lys Asp Pro Lys Arg Leu Tyr Arg Ser Arg Lys
            20                  25                  30

Leu Pro Val Glu Leu Pro Leu Ile Lys Met Lys Pro Val Glu Leu Glu
        35                  40                  45

Ser Ser His Pro Ile Phe His Arg Gly Glu Phe Ser Val Cys Asp
    50                  55                  60

Ser Val Ser Val Trp Val Gly Asp Lys Thr Thr Ala Thr Asp Ile Lys
65                  70                  75                  80

Gly Lys Glu Val Met Val Leu Gly Glu Val Asn Ile Asn Asn Ser Val
                85                  90                  95

Phe Lys Gln Tyr Phe Phe Glu Thr Lys Cys Arg Asp Pro Asn Pro Val
            100                 105                 110

Asp Ser Gly Cys Arg Gly Ile Asp Ser Lys His Trp Asn Ser Tyr Cys
        115                 120                 125

Thr Thr Thr His Thr Phe Val Lys Ala Leu Thr Met Asp Gly Lys Gln
    130                 135                 140

Ala Ala Trp Arg Phe Ile Arg Ile Asp Thr Ala Cys Val Cys Val Leu
145                 150                 155                 160

Ser Arg Lys Ala Val Arg Glx
                165

<210> SEQ ID NO 21
<211> LENGTH: 462
<212> TYPE: DNA
<213> ORGANISM: Artificial sequence
<220> FEATURE:
<223> OTHER INFORMATION: Nucleotide sequence encoding fusion protein

<400> SEQUENCE: 21
gaattcccat ggcatatgaa agacccgaaa cgtctgtacc gttctcgtaa actgcccgtg    60
gaactgccgc tgatcaaaat gaaacccgtg gaactcgaga gctcttccca cccgattttc   120
catcgtggcg agttctccgt gtgtgactct gtctctgtat gggtaggcga taaaaccact   180
gccactgata tcaaaggcaa agaggtgatg gtgctgggag aagtaaacat taacaactct   240
gtattcaaac agtacttctt cgaaactaag tgccgtgacc cgaacccggt agactctggg   300
tgtcgcggca tcgattctaa acactggaac tcttactgca ccactactca cactttcgtt   360
aaagcgttga ctatggatgg taaacaggct gcctggcgtt tcatccgtat cgatactgca   420
tgcgtgtgtg tactgtcccg taaagctgtt cgttaaggat cc                     462

<210> SEQ ID NO 22
<211> LENGTH: 6
<212> TYPE: PRT
<213> ORGANISM: Homo sapiens

<400> SEQUENCE: 22

Leu Ile Lys Met Lys Phe
```

```
1               5
```

<210> SEQ ID NO 23
<211> LENGTH: 6
<212> TYPE: PRT
<213> ORGANISM: Homo sapiens

<400> SEQUENCE: 23

```
Asn Phe Lys Ser Gln Leu
1               5
```

<210> SEQ ID NO 24
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 24

```
Gly Pro Leu Ala Leu Thr Ala Leu
1               5
```

<210> SEQ ID NO 25
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 25

```
Pro Phe Glu Leu Arg Ala
1               5
```

<210> SEQ ID NO 26
<211> LENGTH: 4
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: AMIDATION

<400> SEQUENCE: 26

```
Ala Ala Phe Ala
1
```

<210> SEQ ID NO 27
<211> LENGTH: 8
<212> TYPE: PRT
<213> ORGANISM: Homo sapiens

<400> SEQUENCE: 27

```
Gly Phe Leu Gly Ile Ala Gly Phe
1               5
```

<210> SEQ ID NO 28
<211> LENGTH: 8
<212> TYPE: PRT
<213> ORGANISM: Homo sapiens

```
<400> SEQUENCE: 28

Phe His Tyr Gly Arg Ser Gly Gly
1               5

<210> SEQ ID NO 29
<211> LENGTH: 9
<212> TYPE: PRT
<213> ORGANISM: Homo sapiens

<400> SEQUENCE: 29

Phe Gly Ser Gly Arg Ser Arg Ser Gly
1               5
```